(12) United States Patent
Fonseca et al.

(10) Patent No.: US 10,856,801 B2
(45) Date of Patent: Dec. 8, 2020

(54) SYSTEM AND METHOD FOR SLOW WAVE SLEEP DETECTION

(71) Applicant: KONINKLIJKE PHILIPS N.V., Eindhoven (NL)

(72) Inventors: Pedro Miguel Fonseca, Borgerhout (BE); Xi Long, Eindhoven (NL); Nicolaas Gregorius Petrus Den Teuling, Eindhoven (NL); Reinder Haakma, Eindhoven (NL); Ronaldus Maria Aarts, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 726 days.

(21) Appl. No.: 15/536,158

(22) PCT Filed: Dec. 10, 2015

(86) PCT No.: PCT/IB2015/059508
§ 371 (c)(1),
(2) Date: Jun. 15, 2017

(87) PCT Pub. No.: WO2016/097947
PCT Pub. Date: Jun. 23, 2016

(65) Prior Publication Data
US 2017/0360363 A1 Dec. 21, 2017

Related U.S. Application Data

(60) Provisional application No. 62/093,431, filed on Dec. 18, 2014.

(51) Int. Cl.
A61B 5/00 (2006.01)
G16H 40/63 (2018.01)
(Continued)

(52) U.S. Cl.
CPC ............ *A61B 5/4812* (2013.01); *A61B 5/024* (2013.01); *A61B 5/08* (2013.01); *A61B 5/4806* (2013.01);
(Continued)

(58) Field of Classification Search
CPC ......... A61B 5/024; A61B 5/0476; A61B 5/08; A61B 5/4806; A61B 5/4812;
(Continued)

(56) References Cited

U.S. PATENT DOCUMENTS

2005/0080349 A1 4/2005 Okada et al.
2006/0111635 A1* 5/2006 Todros ................. A61B 5/0402
600/484
(Continued)

FOREIGN PATENT DOCUMENTS

CN 200987667 Y 12/2007
JP 2001008915 A 1/2001
(Continued)

OTHER PUBLICATIONS

Kortelainen, J. M., M. O. Mendez, A. M. Bianchi, M. Matteucci, and S. Cerutti. Sleep staging based on signals acquired through bed sensor. IEEE Trans. Inf. Technol. Biomed. 14:776-785, 2010.
(Continued)

*Primary Examiner* — Michael W Kahelin
*Assistant Examiner* — Vynn V Huh

(57) ABSTRACT

The present disclosure pertains to a system configured to detect slow wave sleep and/or non-slow wave sleep in a subject during a sleep session based on a predicted onset time of slow wave sleep and/or a predicted end time of slow wave sleep that is determined based on changes in cardiorespiratory parameters of the subject. Cardiorespiratory parameters in a subject typically begin to change before transitions between non-slow wave sleep and slow wave
(Continued)

sleep. Predicting this time delay between the changes in the cardiorespiratory parameters and the onset and/or end of slow wave sleep facilitates better (e.g., more sensitive and/or more accurate) determination of slow wave sleep and/or non-slow wave sleep.

15 Claims, 4 Drawing Sheets

(51) Int. Cl.
    *G16H 50/20*     (2018.01)
    *A61B 5/024*     (2006.01)
    *A61B 5/08*     (2006.01)
    *A61B 5/0476*     (2006.01)

(52) U.S. Cl.
    CPC .......... *A61B 5/7264* (2013.01); *A61B 5/7275* (2013.01); *G16H 40/63* (2018.01); *G16H 50/20* (2018.01); *A61B 5/0476* (2013.01); *A61B 5/7282* (2013.01)

(58) Field of Classification Search
    CPC ... A61B 5/7264; A61B 5/7275; A61B 5/7282; A61B 5/4815; A61B 5/4809; A61B 5/0205; A61B 5/0816; G16H 40/63; G16H 50/20
    See application file for complete search history.

(56) References Cited

U.S. PATENT DOCUMENTS

| | | | |
|---|---|---|---|
| 2007/0032733 A1* | 2/2007 | Burton | ............... A61B 5/02405 600/509 |
| 2008/0033304 A1 | 2/2008 | Dalal et al. | |
| 2013/0144152 A1 | 6/2013 | Cervantes | |
| 2014/0088378 A1 | 3/2014 | Muzet | |
| 2015/0273177 A1 | 10/2015 | Iizuka | |

FOREIGN PATENT DOCUMENTS

| | | |
|---|---|---|
| JP | 2008068018 A | 3/2008 |
| WO | 2014167457 A1 | 6/2013 |

OTHER PUBLICATIONS

F. Jurysta, P. van de Borne, P. F. Migeotte, M. Dumont, J. P. Lanquart, J. P. Degaute, and P. Linkowski, "A study of the dynamic interactions between sleep EEG and heart rate variability in healthy young men," Clin. Neurophysiol., vol. 114, No. 11, pp. 2146-2155, Nov. 2003.

Long, X., P. Fonseca, J. Foussier, R. Haakma, and R. Aarts. Sleep and Wake Classification with Actigraphy and Respiratory Effort Using Dynamic Warping. IEEE J. Biomed. Heal. informatics , 2013.

Lafferty, J., A. Mccallum, and F. C. N. Pereira. Conditional random fields: Probabilistic models for segmenting and labeling sequence data. In: Proc. 18th Int. Conf. Mack Learn., 2001.

Willemen, T., D. Van Deun, V. Verhaert, M. Vandekerckhove, V. Exadaktylos, J. Verbraecken, S. Van Huffel, B. Haex, and J. Vander Sloten. An evaluation of cardio-respiratory and movement features with respect to sleep stage classification. IEEE J. Biomed. Heal. informatics , 2013.

Devot, S., R. Dratwa, and E. Naujokat. Sleep/wake detection based on cardiorespiratory signals and actigraphy. In: Proc. 2010 Annu. Int. Conf. IEEE Eng. Med. Biol. Soc., 2010.

\* cited by examiner

SYSTEM AND METHOD FOR SLOW WAVE SLEEP DETECTION

CROSS-REFERENCE TO PRIOR APPLICATIONS

This application is the U.S. National Phase application under 35 U.S.C. § 371 of International Application Serial No. PCT/IB2015/059508, filed on 10 Dec. 2015, which claims the benefit of U.S. Application Ser. No. 62/093,431, filed on 18 Dec. 2014. These applications are hereby incorporated by reference herein.

BACKGROUND

1. Field

The present disclosure pertains to a system and method for detecting slow wave sleep and/or non-slow wave sleep in a subject during a sleep session based on a predicted onset time and/or predicted end time of slow wave sleep determined based on changes in cardiorespiratory parameters of the subject.

2. Description of the Related Art

Assessment of sleep quality based on monitoring sleep and wake phases during bedtime is known. Over-night electroencephalography (EEG) recordings with manually scored hypnograms (done by sleep technicians) for analysis of sleep architecture and occurrence of specific sleep-related problems are known. Manual sleep staging is a time-consuming task that requires the help of a sleep technician. Sensors used during overnight EEG are disruptive of sleep and often require care to apply correctly (e.g., requiring the help of the sleep technician). Typical systems facilitate sleep stage determination for a current epoch of time within a sleep session based on information determined for only that current epoch of time.

SUMMARY

Accordingly, one or more aspects of the present disclosure relate to a system configured to detect slow wave sleep in a subject during a sleep session. The system comprises one or more sensors, one or more physical computer processors, and/or other components. The one or more sensors are configured to generate output signals conveying information related to one or more of cardiac activity of the subject or respiratory activity of the subject; and polysomnography information related to the subject. The one or more physical computer processors are configured by computer readable instructions to: determine one or more cardiorespiratory parameters of the subject over time during the sleep session based on the output signals, the cardiorespiratory parameters including one or more parameters related to the cardiac activity of the subject and/or the respiratory activity of the subject; determine one or more polysomnography parameters of the subject over time during the sleep session based on the output signals; detect changes in the cardiorespiratory parameters over time that are indicative of onset of slow wave sleep in the subject; predict an upcoming onset time of slow wave sleep in the subject based on the detected changes in the cardiorespiratory parameters; and detect slow wave sleep in the subject based on the predicted onset time and the polysomnography parameters, wherein detection is more sensitive during a period of time following the predicted onset time. In some embodiments, the one or more physical computer processors are configured to detect changes in the cardiorespiratory parameters over time that are indicative of an end of slow wave sleep in the subject; predict an upcoming end time of slow wave sleep in the subject based on the detected changes in the cardiorespiratory parameters indicative of the end of slow wave sleep; and detect non-slow wave sleep in the subject based on the predicted end time and the polysomnography parameters, wherein detection of non-slow wave sleep is more sensitive during a period of time following the predicted end time.

Another aspect of the present disclosure relates to a method for detecting slow wave sleep in a subject during a sleep session with a detection system. The detection system comprises one or more sensors, one or more physical computer processors, and/or other components. The method comprises generating, with the one or more sensors, output signals conveying: information related to one or more of cardiac activity of the subject or respiratory activity of the subject; and polysomnography information related to the subject. The method comprises determining, with the one or more physical computer processors, one or more cardiorespiratory parameters of the subject over time during the sleep session based on the output signals, the cardiorespiratory parameters including one or more parameters related to the cardiac activity of the subject and/or the respiratory activity of the subject; determining, with the one or more physical computer processors, one or more polysomnography parameters of the subject over time during the sleep session based on the output signals; detecting, with the one or more physical computer processors, changes in the cardiorespiratory parameters over time that are indicative of onset of slow wave sleep in the subject; predicting, with the one or more physical computer processors, an upcoming onset time of slow wave sleep in the subject based on the detected changes in the cardiorespiratory parameters; and detecting, with the one or more physical computer processors, slow wave sleep in the subject based on the predicted onset time and the polysomnography parameters, wherein the detecting is more sensitive during a period of time following the predicted onset time. In some embodiments, the method comprises detecting, with the one or more physical computer processors, changes in the cardiorespiratory parameters over time that are indicative of an end of slow wave sleep in the subject; predicting, with the one or more physical computer processors, an upcoming end time of slow wave sleep in the subject based on the detected changes in the cardiorespiratory parameters indicative of the end of slow wave sleep; and detecting, with the one or more physical computer processors, non-slow wave sleep in the subject based on the predicted end time and the polysomnography parameters, wherein detection of non-slow wave sleep is more sensitive during a period of time following the predicted end time.

Still another aspect of the present disclosure relates to a system for detecting slow wave sleep in a subject during a sleep session. The system comprises means for generating output signals conveying: information related to one or more of cardiac activity of the subject or respiratory activity of the subject; and polysomnography information related to the subject. The system comprises: means for determining one or more cardiorespiratory parameters of the subject over time during the sleep session based on the output signals, the cardiorespiratory parameters including one or more parameters related to the cardiac activity of the subject and/or the respiratory activity of the subject; means for determining one or more polysomnography parameters of the subject over time during the sleep session based on the output signals; means for detecting changes in the cardiorespiratory parameters over time that are indicative of onset of slow wave sleep in the subject; means for predicting an upcoming onset time of slow wave sleep in the subject based on the detected changes in the cardiorespiratory parameters; and means for detecting slow wave sleep in the subject based on the predicted onset time and the polysomnography parameters, wherein the detecting is more sensitive during a period of time following the predicted onset time. In some embodiments, the system comprises means for detecting changes in the cardiorespiratory parameters over time that are indicative of an end of slow wave sleep in the subject; means for predicting an upcoming end time of slow wave sleep in the subject based on the detected changes in the cardiorespiratory parameters indicative of the end of slow wave sleep; and means for detecting non-slow wave sleep in the subject based on the predicted end time and the polysomnography parameters, wherein detection of non-slow wave sleep is more sensitive during a period of time following the predicted end time.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
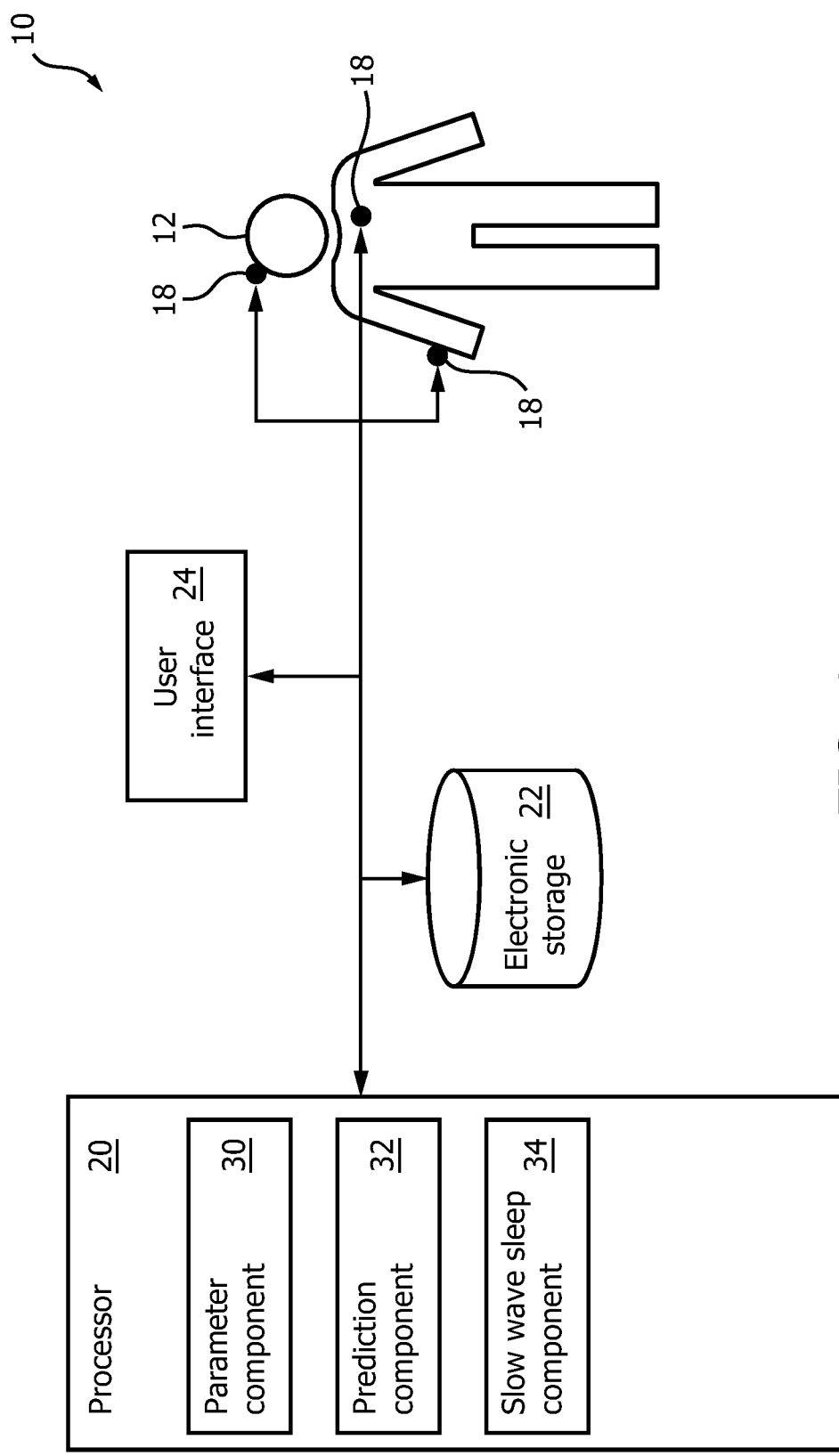
FIG. 1 illustrates a system configured to detect slow wave sleep in a subject during a sleep session based on a predicted onset time of slow wave sleep that is determined based on changes in cardiorespiratory parameters of the subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to detect slow wave sleep in a subject 12 during a sleep session. Slow wave sleep is detected based on a predicted onset time of slow wave sleep that is determined based on changes in cardiorespiratory parameters of subject 12 and/or other information. Cardiorespiratory parameters in subject 12 typically begin to change before the onset of slow wave sleep (e.g., before transitions between non-slow wave sleep and slow wave sleep). Predicting this time delay between the changes in the cardiorespiratory parameters and the onset of slow wave sleep facilitates better (e.g., more sensitive and/or more accurate) determination of slow wave sleep. Slow wave sleep may be and/or may be associated with non-rapid eye movement (NREM) sleep (e.g., including stage N3 sleep), and/or other sleep in subject 12. In some embodiments, system 10 is configured to detect non-slow wave sleep (e.g., REM and or other non-slow wave sleep) in subject 12 based on a predicted end time of slow wave sleep. The end time is predicted based on changes in cardiorespiratory parameters that start occurring before the end of slow wave sleep in subject 12 and are indicative of an upcoming transition to non-slow wave sleep.

The use of cardiorespiratory parameters to predict the onset (and/or an end) of slow wave sleep provides a promising alternative and/or compliment to using only EEG parameters to determine sleep stages because cardiorespiratory parameters may be measured using unobtrusive methods and/or sensors (described below) and because the cardiorespiratory parameters can be used to predict upcoming slow wave sleep in subject 12 (whereas EEG parameters from a specific epoch of time are used to determine the sleep stage for that epoch of time). System 10 is advantageous because sleep is a structured process in which parameters determined for individual epochs of time during a sleep session are not independent over time. In some embodiments, system 10 includes one or more of a sensor 18, a processor 20, electronic storage 22, user interface 24, and/or other components.

Sensor 18 is configured to generate output signals conveying information related to cardiac activity of subject 12, respiratory activity of subject 12, polysomnography information related to subject 12, and/or other information. The cardiac activity of subject 12, respiratory activity of subject 12, and/or polysomnography information related to subject 12 may correspond to a sleep stage of subject 12 and/or other characteristics of subject 12. For example, the cardiac and/or respiratory activity of subject 12 may be predictive of upcoming sleep stages in subject 12. The polysomnography information may be indicative of a current sleep stage in subject 12. The sleep stage of subject 12 may be associated with rapid eye movement (REM) sleep, non-rapid eye movement (NREM) sleep, and/or other sleep.

Sensors 18 may comprise one or more sensors that generate output signals that convey information related to cardiac activity in subject 12, respiratory activity in subject 12, and/or polysomnography information related to subject 12 directly and/or indirectly. For example, one or more sensors 18 may generate an output based on a heart rate of subject 12 (e.g., sensors 18 may be and/or include a heart rate sensor located on the chest of subject 12, and/or be configured as a bracelet on a wrist of subject 12, and/or be located on another limb of subject 12), movement of subject 12 (e.g., sensors 18 may include a bracelet around the wrist and/or ankle of subject 12 with an accelerometer such that sleep may be analyzed using actigraphy signals), respiration of subject 12, and/or other characteristics of subject 12. In some embodiments, sensors 18 include sensors used to determine heart rate (and/or other cardiac parameters) that are contactless, for example, and include piezoelectric sensors on and/or under a bed mattress, strain gauges installed on bed slats, load cells under the bed feet, accelerometers in a pillow and/or on the mattress configured to measure longitudinal (along the direction of the bed) accelerations, which can be used to measure cardiac activity by ballistocardiography and/or other techniques. As another example, one or more sensors 18 that generate polysomnography information may include electroencephalogram (EEG) electrodes configured to detect electrical activity along the scalp of subject 12 resulting from current flows within the brain of subject 12. In some embodiments, the polysomnography information may include the information related to cardiac activity of subject 12 (e.g., heart rhythm (ECG and/or EKG) information), the information related to respiratory activity of subject 12, eye movement information (EOG), muscle activity and/or skeletal muscle activation (EMG) information, and/or other information.

Although sensors 18 are illustrated at three individual locations on subject 12, this is not intended to be limiting. Sensors 18 may include sensors disposed in a plurality of locations, such as for example, within (or in communication with) user interface 24, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device, or processor 20 may represent processing functionality of a plurality of devices operating in coordination.

As shown in FIG. 1, processor 20 is configured to execute one or more computer program components. The one or more computer program components may comprise one or more of a parameter component 30, a prediction component 32, a slow wave sleep component 34, and/or other components. Processor 20 may be configured to execute components 30, 32, and/or 34 by software; hardware; firmware; some combination of software, hardware, and/or firmware; and/or other mechanisms for configuring processing capabilities on processor 20.

It should be appreciated that although components 30, 32, and 34 are illustrated in FIG. 1 as being co-located within a single processing unit, in embodiments in which processor 20 comprises multiple processing units, one or more of components 30, 32, and/or 34 may be located remotely from the other components. The description of the functionality provided by the different components 30, 32, and/or 34 described below is for illustrative purposes, and is not intended to be limiting, as any of components 30, 32, and/or 34 may provide more or less functionality than is described. For example, one or more of components 30, 32, and/or 34 may be eliminated, and some or all of its functionality may be provided by other components 30, 32, and/or 34. As another example, processor 20 may be configured to execute one or more additional components that may perform some or all of the functionality attributed below to one of components 30, 32, and/or 34.

Parameter component 30 is configured to determine one or more parameters in system 10. Parameter component 30 is configured to determine the one or more parameters based on the output signals from sensors 18, information entered, selected, and/or otherwise received via user interface 24, information stored in electronic storage 22, and/or other information. In some embodiments, the parameters may include features extracted from the information conveyed by the output signals from sensors 18. In some embodiments, the parameters may include parameters determined based on one or more other previously determined parameters (e.g., averages, standard deviations, an area under a curve, a maximum, a minimum, a median, etc.). In some embodiments, determining one or more parameters includes determining one or more parameters for the whole sleep session, determining one or more parameters in an ongoing way for the sleep session, determining one or more parameters at one or more individual points time in the sleep session, and/or determining other parameters.

In some embodiments, the parameters include cardiorespiratory parameters of subject 12, polysomnography parameters of subject 12, and/or other parameters. In some embodiments, parameter component 30 is configured to determine one or more cardiorespiratory parameters of subject 12 over time during the sleep session based on the output signals. In some embodiments, the one or more cardiorespiratory parameters include cardiac activity parameters, respiratory parameters, cardiorespiratory coupling parameters, and/or other parameters. In some embodiments, the cardiac activity parameters include parameters related to and/or determined based on an electrocardiogram (EKG) of subject 12, and/or other parameters. In some embodiments, the cardiac activity parameters include parameters related to and/or determined based on a ballistocardiogram (BCG) of subject 12. A BCG can be measured in a contactless way, for example, with piezoelectric sensors on or under the bed mattress, strain gauges installed on bed slats, load cells under the bed feet, accelerometers in the pillow or on the mattress, configured to measure longitudinal (along the direction of the bed) accelerations. In some embodiments the cardiac activity parameters include parameters related to and/or determined based on a photoplethysmograph (PPG) of subject 12. PPG can be measured in reflective (measuring the amount of scattered/reflected light on the skin) or transmissive (measuring the amount of light transmitted through the skin) way, and mounted on the body of the subject (e.g. on the wrist, on the finger, on the forehead, in the ear, etc), or remotely (e.g. with a video camera directed at exposed skin of the subject, configured to measure changes in color associated with changes in blood volume on that area). In some embodiments, the cardiac activity parameters may include parameters determined based on statistics computed over R-R intervals, such as the number of intervals per epoch (e.g., expressing the average heart rate in that epoch), the nth percentile, the standard deviation and/or the range of the interval lengths, and/or other parameters. In some embodiments, the cardiac activity parameters include a heart rate, a blood pressure, a voltage, oxygen saturation, and/or other parameters.

In some embodiments, the respiratory parameters may include parameters indicative of respiratory effort, airflow, ventilation, and/or respiration measured by other contact sensors (e.g. respiratory inductance plethysmograph around the chest or abdomen of the subject, or accelerometers mounted on the chest of the subject), or non-contact/unobtrusive devices (e.g. with piezoelectric sensors on or under the bed mattress, strain gauges installed on bed slats, load cells under the bed feet, accelerometers in the pillow or on the mattress, configured to measure accelerations perpendicular to the direction of the bed) in subject 12, a respiration rate of subject 12, a flow rate (e.g., of gas into and out of subject 12 during respiration), a volume (e.g., a tidal volume of inhaled and/or exhaled gas), a pressure (e.g., an inhalation pressure, an exhalation pressure), an amplitude (e.g., of pressure and/or any other parameter of inhaled and/or exhaled gas), and/or other parameters. In some embodiments, the respiration parameters may include a parameter indicative of variation in the respiration rate of subject 12 (and/or variation of any respiration parameter) for the sleep session.

Parameter component 30 is configured such that cardiorespiratory coupling parameters express a strength of a coupling between the cardiac and the respiratory autonomic systems of subject 12. The strength of this link depends on the sleep stage of subject 12. Cardiorespiratory coupling/interaction parameters may describe a relationship between R-R intervals and a respiratory phase (e.g., inhalation/exhalation) of subject 12 during a number of breathing cycles. For example, cardiorespiratory coupling parameters may include a percentage of phase-synchronized period, a ratio between the number of heart beats to breathing cycles, and/or other parameters.

In some embodiments, parameter component 30 is configured to determine one or more polysomnography parameters of subject 12 over time during the sleep session based on the output signals. The polysomnography parameters may include parameters related to electrical signals from neurons of the cortex of subject 12 (e.g., EEG parameters), eye activity parameters (e.g., EOG parameters), muscle activity parameters and/or skeletal muscle activation (e.g., EMG parameters), electrocardiogram (e.g., ECG and/or EKG) parameters, and/or other parameters. In some embodiments, the cardiorespiratory parameters may be included in the polysomnography parameters.

In some embodiments, prediction component 32 is configured to detect changes in one or more of the cardiorespiratory parameters and/or other parameters over time for the sleep session. The changes in the cardiorespiratory parameters may include changes over time that are indicative of onset of slow wave sleep in subject 12. The changes in the cardiorespiratory parameters may include changes over time that are indicative of an end of slow wave sleep. In some embodiments, the changes in the cardiorespiratory parameters over time that are indicative of onset of slow wave sleep in subject 12 include changes in the cardiorespiratory parameters that breach corresponding slow wave sleep onset threshold levels for the cardiorespiratory parameters. In some embodiments, the changes in the cardiorespiratory parameters over time that are indicative of and end of slow wave sleep in subject 12 include changes in the cardiorespiratory parameters that breach corresponding slow wave sleep end threshold levels for the cardiorespiratory parameters. The slow wave sleep onset and/or end threshold levels may include one or more predetermined threshold levels and/or one or more threshold levels determined based on previous sleep of subject 12 and/or other information, for example. In some embodiments, the slow wave sleep onset and/or end threshold levels may be determined at manufacture, obtained via information entered and/or received via user interface 24, and/or determined in other ways. In some embodiments, the slow wave sleep onset and/or end threshold levels may be adjusted by prediction component 32 based on previous sleep of subject 12, information entered and/or received via user interface 24, and/or other information. In some embodiments, threshold levels may be determined relative to a current level of one or more of the cardiorespiratory parameters, for example. Changes in one or more of the cardiorespiratory parameters that are indicative of onset and/or end of slow wave sleep in subject 12 may include, for example, the heart rate of subject 12 decreasing (onset) and/or increasing (end), the standard deviation of inter-beat intervals decreasing (onset) and/or increasing (end), changes in the power in a very-low frequency (VLF), a low frequency (LF), and a high frequency (HF) band of a heart rate signal over R-R intervals, a decrease (onset) and/or increase (end) of standard deviation of respiratory frequency, increases (onset) and/or decreases (end) of regularity and self-similarity on respiratory signal morphology and its envelope, an enhancement (onset) of cardiorespiratory coupling (or phase synchronization), and/or other changes.

Prediction component 32 is configured to predict an upcoming onset time and/or end time of slow wave sleep in subject 12. The onset and/or end time is predicted based on the detected changes in the cardiorespiratory parameters and/or other information. In some embodiments, the upcoming onset time is a time delay between a time the changes in the cardiorespiratory parameters that are indicative of onset of slow wave sleep in the subject are detected and a time slow wave sleep occurs in the subject. In some embodiments, the upcoming end time is a time delay between a time the changes in the cardiorespiratory parameters that are indicative of and end of slow wave sleep in the subject are detected and a time non-slow wave sleep occurs in the subject. In some embodiments, the predicted onset and/or end time is an upcoming time of day. In some embodiments, the duration (e.g., length) of the delay and/or the length of time until the predicted onset and/or end time of day is predicted based on changes in the levels of one or more of the parameters (e.g., based on how much a parameter changed), a rate of change in the levels of the parameters, and/or other information.

In some embodiments, prediction component 32 is configured to obtain baseline onset and/or end time delay information for a population of subjects. The baseline onset and/or end time delay information may indicate an aggregated amount of time between changes in cardiorespiratory parameters and an onset and/or end of slow wave sleep for the population of subjects. In some embodiments, prediction component 32 is configured such that predicting the upcoming onset and/or end time of slow wave sleep in subject 12 is based on the detected changes in the cardiorespiratory parameters and/or the baseline onset and/or end time delay information.

Slow wave sleep component 34 is configured to detect slow wave sleep in subject 12. Slow wave sleep is detected based on the predicted onset time the, the output signals, the cardiorespiratory parameters, the polysomnography parameters, and/or other information. In some embodiments, slow wave sleep component 34 may determine the current sleep stage of subject 12 (e.g., whether subject 12 is in slow wave sleep) based on an analysis of the polysomnography information conveyed by the output signals of sensor 18, the polysomnography parameters determined by parameter component 30, and/or other polysomnography information. The analysis may include generating and/or monitoring a polysomnogram for the sleep session of subject 12. In some embodiments, the analysis may include transforming one or more of the output signals into a frequency domain. In some embodiments, the analysis may include detecting slow wave sleep based on power in one or more frequency bands of the polysomnogram (e.g., of the transformed output signals). In some embodiments, slow wave sleep may be detected responsive to power in one or more of these frequency bands breaching slow wave sleep thresholds for the power and/or particular frequency bands. Similarly, in some embodiments, slow wave sleep component 34 is configured to detect non-slow wave sleep in subject 12 (e.g., using the predicted end time instead of the predicted onset time).

In some embodiments, slow wave sleep component 34 is configured such that the detecting is more sensitive during a period of time following the predicted onset time. This may include adjusting one or more of the thresholds used to detect slow wave sleep, changing the analysis of the polysomnogram (e.g., determining more or less parameters for one or more of the frequency bands during the period of time), and/or other actions that facilitate detection of slow wave sleep during a period of time following the predicted onset time. In some embodiments, detecting slow wave sleep in subject 12 based on the predicted onset time and the polysomnography parameters includes enabling detection during the period of time following the predicted onset time. This may include performing the analysis of the polysomnogram to detect slow wave sleep only during the period of time following the predicted onset time, for example. In some embodiments, making detection more sensitive and/or enabling detection during a period of time following the predicted onset time may be thought of as "looking for" slow wave sleep in subject 12. Slow wave sleep component 34 may be configured to "look for" slow wave sleep during a period of time following the predicted onset time of slow wave sleep because it is more likely (e.g., the changing cardiorespiratory parameters predict) that subject 12 will be in slow wave sleep at that time. System 10 may be less sensitive to slow wave sleep at other times because the cardiorespiratory parameters have not indicated an upcoming period of slow wave sleep. By way of a non-limiting example, changing cardiorespiratory parameters in subject 12 (e.g., as detected by prediction component 32) may indicate an upcoming period of slow wave sleep. Prediction component 32 may predict that the slow wave sleep will occur in about 2.5 minutes. After the 2.5 minutes has elapsed, slow wave sleep component 34 may "look for" (e.g., enable slow wave sleep detection and/or make slow wave sleep detection more sensitive as described above) slow wave sleep in subject 12.

Similarly, in some embodiments, slow wave sleep component 34 is configured such that the detecting non-slow wave sleep is more sensitive during a period of time following the predicted end time. This may include adjusting one or more of the thresholds used to detect non-slow wave sleep, changing the analysis of the polysomnogram (e.g., determining more or less parameters for one or more of the frequency bands during the period of time), and/or other actions that facilitate detection of non-slow wave sleep during a period of time following the predicted end time. In some embodiments, detecting non-slow wave sleep in subject 12 based on the predicted end time and the polysomnography parameters includes enabling detection during the period of time following the predicted end time. This may include performing the analysis of the polysomnogram to detect non-slow wave sleep only during the period of time following the predicted end time, for example. In some embodiments, making detection more sensitive and/or enabling detection during a period of time following the predicted end time may be thought of as "looking for" non-slow wave sleep in subject 12. Slow wave sleep component 34 may be configured to "look for" non-slow wave sleep during a period of time following the predicted end time of slow wave sleep because it is more likely (e.g., the changing cardiorespiratory parameters predict) that subject 12 will be in non-slow wave sleep at that time.

Figure 2:
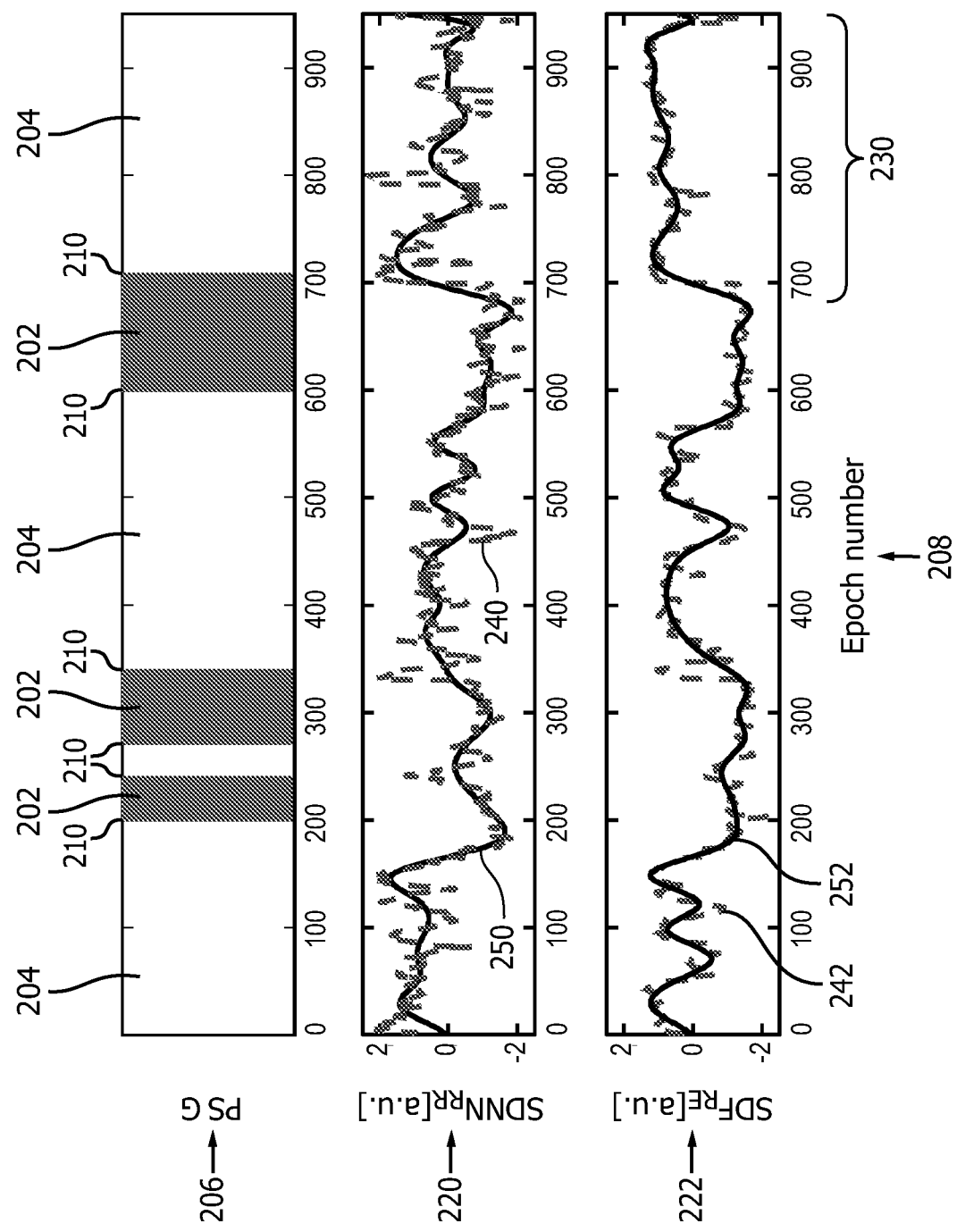
FIG. 2 illustrates slow wave and non-slow wave sleep determined based on polysomnography parameters for multiple epochs of time during a sleep session. The slow wave and the non-slow wave sleep are illustrated side by side with two cardiorespiratory parameters.

FIG. 2 illustrates an example of slow wave 202 and non-slow wave 204 sleep determined based on polysomnography parameters (PSG) 206 for multiple epochs of time 208 during a sleep session. Slow wave 202 and non-slow wave 204 sleep are illustrated side by side with two cardiorespiratory parameters 220 and 222. Unsmoothed (dashed) 240, 242 and smoothed (solid) 250, 252 parameter values of parameters 220 and 222 are plotted. Without system 10 (FIG. 1), errors in sleep stage classification (e.g., slow wave sleep 202 versus non-slow wave sleep 204) are likely to occur at or near the transitions 210 between slow wave sleep 202 and non-slow wave sleep 204, particularly for later epochs of time 230 (e.g., during the second half of a night of sleep around the transition at the 700th epoch).

Figure 3:
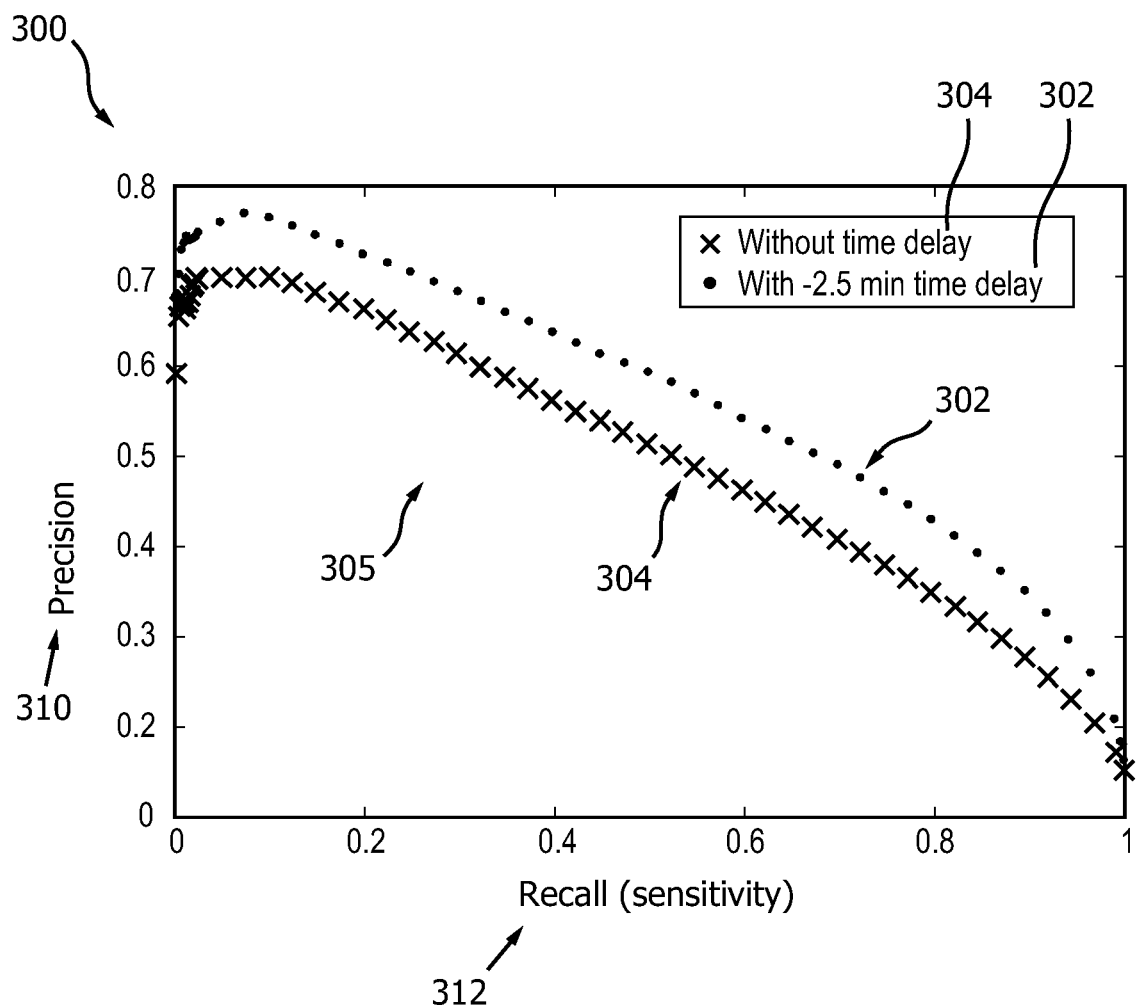
FIG. 3 illustrates results from experimentation performed with and without the present system.

FIG. 3 illustrates results 300 from experimentation performed with 302 and without 304 using system 10 (FIG. 1). FIG. 3 illustrates sleep stage detection results with and without using a predicted time delay (e.g., the predicted onset time of slow wave sleep determined by prediction component 32 shown in FIG. 1). FIG. 3 illustrates pooled PR curves of slow wave sleep detection with and without using a 2.5 min predicted time delay. To generate the data illustrated in FIG. 3, full PSG information (e.g., at least 16 PSG channels of bio-signals) was collected from 165 healthy adults in the SIESTA project. The project was supported by the European Commission and the subjects were monitored in seven different sleep centers located in five European countries over a period of three years from 1997 to 2000. A subject was considered "healthy" when the Pittsburgh Sleep Quality Index (PSQI) scored less than 6 and fulfilled several criteria such as no shift work, no depressive symptoms, and a usual bedtime before midnight. According to the SIESTA protocol, all of the subjects spent two consecutive nights in the sleep laboratories, resulting in a total of 330 over-night PSG information recordings. For an individual recording, the scoring of sleep stages was carried out by sleep clinicians based on the PSG channels according to the R&K rules. Stages were scored for 30 second epochs as wake, REM, and S1-S4 for NREM sleep (S1-S4 may correspond to and/or be the same as stages N1-N3 described above). In order to train and test system 10 (FIG. 1), wake, REM, S1, and S2 were merged into a single non-slow wave sleep class; S3 and S4 were grouped as a single slow wave sleep class. Normal humans typically have a total slow wave sleep time of approximately 30-200 min over an entire night of sleep (e.g., a sleep session). Thus, the focus of the experiment was on recordings having a total slow wave sleep time of not less than 30 min. This resulted in a smaller 'normal' group of 257 recordings (from 145 subjects). Table I summarizes the subject demographics and some parameters of the normal subjects. In this experiment, the thoracic respiratory effort signal (sampled at 10 Hz) was acquired with inductance plethysmography and the cardiac signal (sampled at 512 Hz) was recorded with lead II ECG.

TABLE I

| Parameter | Mean ± Std | Range |
| --- | --- | --- |
| Recordings | N = 257 (145 subjects) | |
| Sex | 65 males and 80 females | |
| Age [year] | 49.5 ± 19.2 | 20-95 |
| BMI | 24.3 ± 3.4 | 17.0-34.8 |
| Total recording time | 7.8 ± 0.5 | 5.7-9.3 |
| SWS [%] | 14.8 ± 5.1 | 6.2-32.2 |

Cardiorespiratory parameters used to predict upcoming onset of slow wave sleep can be selected and/or determined using a feature selector, such as a correlation-based feature selection (CFS) method, yielding a total of 6 features when all cardiorespiratory parameters were considered. They were (these features are just examples, and this prediction scheme with 'time delay' can be applied to any features):

$SDNN_{RR}$: RR standard deviation;
$LF_{RR}$: RR spectrum power in LF band;
$DFA_{RR}$: detrended fluctuation analysis (parameter a);
$SDF_{RE}$: respiratory frequency standard deviation;
$SDMT_{RE}$: respiratory trough standardized median; and
$SDMP_{RE}$: respiratory peak standardized median.

Conventional metrics of overall accuracy, precision, sensitivity, and specificity were first considered to evaluate system 10. However, such metrics were not be the most appropriate criteria for the "imbalanced class distribution" here, where the non-slow wave sleep epochs account for an average of 85.2% of the recording which is much larger than that of slow wave sleep epochs, accounting for only 14.8%. The Cohen's Kappa coefficient of agreement κ offered a more insightful indication of the general classification performance in correctly identifying both classes (slow wave sleep and non-slow wave sleep) which are imbalanced, while compensating for the probability of chance agreement. Note that here a slow wave/non-slow wave classifier threshold was chosen to optimize the pooled Kappa. To obtain an overview of the sleep stage classification performance of system 10 across the entire solution space, a Precision-Recall (PR) curve 305 was used. A precision recall curve plots precision 310 versus recall (or sensitivity) 312 by varying the sleep stage classifier threshold used to separate the two classes. Instead of the well-known Receiver Operating Characteristic (ROC) curve which has been shown to be over-optimistic when the data is heavily imbalanced between classes, a PR curve provides a more conservative measure of a sleep stage classifier's (such as system 10) performance. When comparing classifiers (e.g., system 10 which uses the predicted onset time compared to systems that do not use a predicted onset time), the metric 'area under the PR curve' (AUCPR) is typically calculated. In general, a larger $AUC_{PR}$ indicates a better classification performance.

The slow wave sleep versus non-slow wave sleep detection results with and without using time delay (e.g., with and without using system 10) are compared in Table II and FIG. 3. A time delay of about −2.5 (this is not intended to be limiting) min was experimentally found to be optimal. It can be seen that the slow wave sleep detection performance can be significantly improved after using the features with negative time delay in Table II and FIG. 3.

TABLE II

| Time delay | Result | Precision [%] | Sensitivity [%] | Specificity [%] | Accuracy [%] | Kappa | $AUC_{PR}$ |
| --- | --- | --- | --- | --- | --- | --- | --- |
| No | Pool | 50.3 | 51.6 | 91.0 | 85.0 | 0.41 | 0.49 |
| | Average | 48.9 ± 16.4 | 52.4 ± 18.7 | 90.9 ± 3.1 | 84.9 ± 4.1 | 0.40 ± 0.16 | 0.50 ± 0.17 |
| Yes | Pool | 55.9 | 56.9 | 92.0 | 86.8 | 0.49 | 0.57 |
| | Average | 54.5 ± 16.4 | 58.1 ± 19.5 | 92.0 ± 2.9 | 86.6 ± 4.1 | 0.47 ± 0.17* | 0.58 ± 0.17* |

*Significance of difference was examined with a Wilcoxon signed-rank test with p < 0.0001.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensors 18, processor 20, and/or other components of system 10. Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 4:
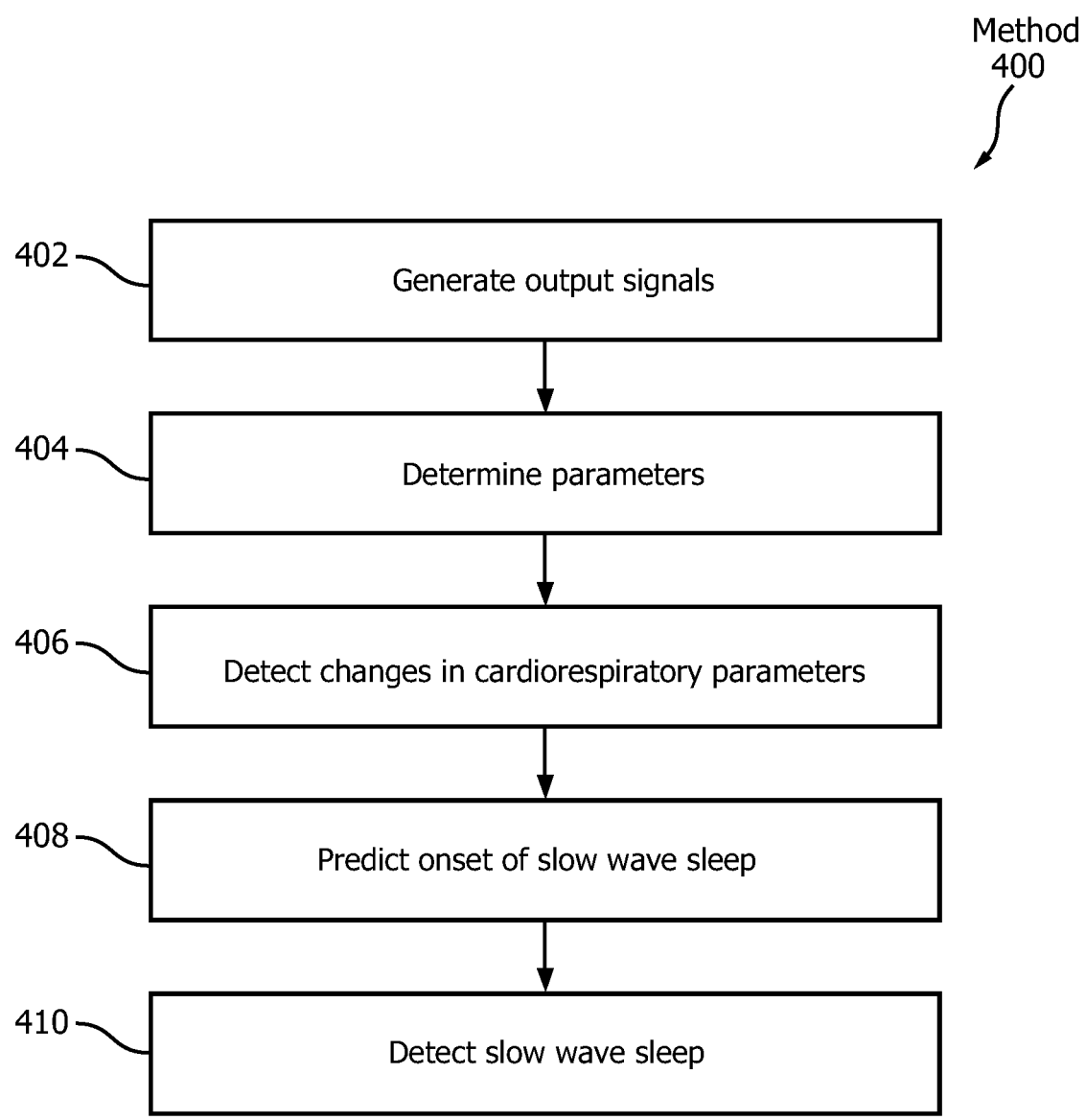
FIG. 4 illustrates a method for detecting slow wave sleep in a subject during a sleep session with the present system.

FIG. 4 illustrates a method 400 for detecting slow wave sleep in a subject during a sleep session with a detection system. The detection system comprises one or more sensors, one or more physical computer processors, and/or other components. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, output signals conveying information related to one or more of cardiac activity of the subject or respiratory activity of the subject; and polysomnography information related to the subject are generated. In some embodiments, operation 402 is performed by one or more sensors the same as or similar to sensors 18 (shown in FIG. 1 and described herein).

At an operation 404, one or more cardiorespiratory parameters and one or more polysomnography parameters of the subject are determined. In some embodiments, operation 404 includes determining one or more cardiorespiratory parameters of the subject over time during the sleep session based on the output signals. The cardiorespiratory parameters include one or more parameters related to the cardiac activity of the subject and/or the respiratory activity of the subject, for example. In some embodiments, operation 404 includes determining one or more polysomnography parameters of the subject over time during the sleep session based on the output signals. In some embodiments, operation 404 is performed by a physical computer processor the same as or similar to processor 20 (shown in FIG. 1 and described herein).

At an operation 406, changes in one or more of the cardiorespiratory parameters are detected. The changes in the cardiorespiratory parameters may include changes over time that are indicative of onset of slow wave sleep in the subject. In some embodiments, the changes in the cardiorespiratory parameters over time that are indicative of onset of slow wave sleep in the subject include changes in the cardiorespiratory parameters that breach corresponding slow wave sleep onset thresholds for the cardiorespiratory parameters. The slow wave sleep onset thresholds may include one or more predetermined thresholds and/or one or more thresholds determined based on previous sleep of the subject, for example. In some embodiments, the detected changes in cardiorespiratory parameters include changes over time that are indicative of an end of slow wave sleep in the subject. Such changes may include changes that breach corresponding slow wave sleep end thresholds, for example. In some embodiments, operation 406 is performed by a physical computer processor the same as or similar to processor 20 (shown in FIG. 1 and described herein).

At an operation 408, an upcoming onset time of slow wave sleep in the subject is predicted. The onset time is predicted based on the detected changes in the cardiorespiratory parameters and/or other information. In some embodiments, the upcoming onset time is a time delay between a time the changes in the cardiorespiratory parameters that are indicative of onset of slow wave sleep in the subject are detected and a time slow wave sleep occurs in the subject. In some embodiments, operation 408 includes obtaining, with the one or more physical computer processors, baseline onset time delay information for a population of subjects. The baseline onset time delay information may indicate an aggregated amount of time between changes in cardiorespiratory parameters and an onset of slow wave sleep for the population of subjects. In some embodiments, predicting the upcoming onset time of slow wave sleep in the subject is based on the detected changes in the cardiorespiratory parameters and the baseline onset time delay information. In some embodiments, instead of and/or in addition to predicting an upcoming onset time of slow wave sleep, operation 408 includes predicting an upcoming end time of slow wave sleep in the subject based on similar information for the end of slow wave sleep. In some embodiments, operation 408 is performed by a physical computer processor the same as or similar to processor 20 (shown in FIG. 1 and described herein).

At an operation 410, slow wave sleep in the subject is detected. Slow wave sleep is detected based on the predicted onset time and the polysomnography parameters. The detecting is more sensitive during a period of time following the predicted onset time. In some embodiments, detecting slow wave sleep in the subject based on the predicted onset time and the polysomnography parameters includes enabling detection during the period of time following the predicted onset time. Similarly, in some embodiments, operation 410 includes detecting non-slow wave sleep in addition to and/or instead of detecting slow wave sleep. In these embodiments, changes in the cardiorespiratory parameters over time that are indicative of an end of slow wave sleep in the subject are detected; an upcoming end time of slow wave sleep in the subject is predicted based on the detected changes in the cardiorespiratory parameters indicative of the end of slow wave sleep; and non-slow wave sleep in the subject is detected based on the predicted end time and the polysomnography parameters, wherein detection of non-slow wave sleep is more sensitive during a period of time following the predicted end time. In some embodiments, operation 410 is performed by a physical computer processor the same as or similar to processor 20 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to detect slow wave sleep in a subject during a sleep session, the system comprising:
   one or more sensors configured to generate output signals conveying:
      information related to one or more of cardiac activity of the subject or respiratory activity of the subject; and
      polysomnography information related to the subject; and
   one or more physical computer processors configured by computer readable instructions to:
      determine one or more cardiorespiratory parameters of the subject over time during the sleep session based on the output signals, the cardiorespiratory parameters including one or more parameters related to the cardiac activity of the subject and/or the respiratory activity of the subject;
      determine one or more polysomnography parameters of the subject over time during the sleep session based on the output signals, wherein the one or more polysomnography parameters include one or more of a heart rhythm (ECG and/or EKG), eye movement (EOG), or skeletal muscle activation (EMG) parameters;
      detect changes in the cardiorespiratory parameters over time that are indicative of onset of slow wave sleep in the subject;
      predict an upcoming onset time of slow wave sleep in the subject based on the detected changes in the cardiorespiratory parameters; and
      detect slow wave sleep in the subject based on the predicted upcoming onset time of slow wave sleep and the polysomnography parameters, wherein detection is more sensitive during a period of time following the predicted upcoming onset time of slow wave sleep.

2. The system of claim 1, wherein the one or more physical computer processors are configured such that detecting slow wave sleep in the subject based on the predicted upcoming onset time of slow wave sleep and the polysomnography parameters includes enabling detection during the period of time following the predicted upcoming onset time of slow wave sleep.

3. The system of claim 1, wherein the one or more physical computer processors are configured such that the upcoming onset time is a time delay between a time the changes in the cardiorespiratory parameters that are indicative of onset of slow wave sleep in the subject are detected and a time slow wave sleep occurs in the subject.

4. The system of claim 1, wherein the one or more physical computer processors are further configured to:
   obtain baseline onset time delay information for a population of subjects, the baseline onset time delay information indicating an aggregated amount of time between changes in cardiorespiratory parameters and an onset of slow wave sleep for the population of subjects; and
   predict the upcoming onset time of slow wave sleep in the subject based on the detected changes in the cardiorespiratory parameters and the baseline onset time delay information.

5. The system of claim 1, wherein the one or more physical computer processors are configured such that the changes in the cardiorespiratory parameters over time include changes in the cardiorespiratory parameters that breach corresponding slow wave sleep onset thresholds for the cardiorespiratory parameters, the slow wave sleep onset thresholds including one or more predetermined thresholds and/or one or more thresholds determined based on previous sleep of the subject.

6. The system of claim 1, wherein the one or more physical computer processors are further configured to:
   detect changes in the cardiorespiratory parameters over time that are indicative of an end of slow wave sleep in the subject;
   predict an upcoming end time of slow wave sleep in the subject based on the detected changes in the cardiorespiratory parameters indicative of the end of slow wave sleep; and
   detect non-slow wave sleep in the subject based on the predicted upcoming end time of slow wave sleep and the polysomnography parameters, wherein detection of non-slow wave sleep is more sensitive during a period of time following the predicted upcoming end time of slow wave sleep.

7. A method for detecting slow wave sleep in a subject during a sleep session with a detection system, the detection system comprising one or more sensors and one or more physical computer processors, the method comprising:
   generating, with the one or more sensors, output signals conveying:
      information related to one or more of cardiac activity of the subject or respiratory activity of the subject; and
      polysomnography information related to the subject;
   determining, with the one or more physical computer processors, one or more cardiorespiratory parameters of the subject over time during the sleep session based on the output signals, the cardiorespiratory parameters including one or more parameters related to the cardiac activity of the subject and/or the respiratory activity of the subject;
   determining, with the one or more physical computer processors, one or more polysomnography parameters of the subject over time during the sleep session based on the output signals, wherein the one or more polysomnography parameters include heart rhythm (ECG and/or EKG), eye movement (EOG), or skeletal muscle activation (EMG) parameters;

detecting, with the one or more physical computer processors, changes in the cardiorespiratory parameters over time that are indicative of onset of slow wave sleep in the subject;

predicting, with the one or more physical computer processors, an upcoming onset time of slow wave sleep in the subject based on the detected changes in the cardiorespiratory parameters; and detecting, with the one or more physical computer processors, slow wave sleep in the subject based on the predicted upcoming onset time of slow wave sleep and the polysomnography parameters, wherein the detecting is more sensitive during a period of time following the predicted upcoming onset time of slow wave sleep.

8. The method of claim 7, wherein detecting slow wave sleep in the subject based on the predicted upcoming onset time of slow wave sleep and the polysomnography parameters includes enabling detection during the period of time following the predicted upcoming onset time of slow wave sleep.

9. The method of claim 7, wherein the upcoming onset time is a time delay between a time the changes in the cardiorespiratory parameters that are indicative of onset of slow wave sleep in the subject are detected and a time slow wave sleep occurs in the subject.

10. The method of claim 7, further comprising:

obtaining, with the one or more physical computer processors, baseline onset time delay information for a population of subjects, the baseline onset time delay information indicating an aggregated amount of time between changes in cardiorespiratory parameters and an onset of slow wave sleep for the population of subjects; and predicting, with the one or more physical computer processors, the upcoming onset time of slow wave sleep in the subject based on the detected changes in the cardiorespiratory parameters and the baseline onset time delay information.

11. The method of claim 7, wherein the changes in the cardiorespiratory parameters over time that are indicative of onset of slow wave sleep in the subject include changes in the cardiorespiratory parameters that breach corresponding slow wave sleep onset thresholds for the cardiorespiratory parameters, the slow wave sleep onset thresholds including one or more predetermined thresholds and/or one or more thresholds determined based on previous sleep of the subject.

12. The method of claim 7, further comprising:

detecting, with the one or more physical computer processors, changes in the cardiorespiratory parameters over time that are indicative of an end of slow wave sleep in the subject;

predicting, with the one or more physical computer processors, an upcoming end time of slow wave sleep in the subject based on the detected changes in the cardiorespiratory parameters indicative of the end of slow wave sleep; and detecting, with the one or more physical computer processors, non-slow wave sleep in the subject based on the predicted upcoming end time of slow wave sleep and the polysomnography parameters, wherein detection of non-slow wave sleep is more sensitive during a period of time following the predicted upcoming end time of slow wave sleep.

13. A system for detecting slow wave sleep in a subject during a sleep session, the system comprising:

means for generating output signals conveying:

information related to one or more of cardiac activity of the subject or respiratory activity of the subject; and polysomnography information related to the subject;

means for determining one or more cardiorespiratory parameters of the subject over time during the sleep session based on the output signals, the cardiorespiratory parameters including one or more parameters related to the cardiac activity of the subject and/or the respiratory activity of the subject;

means for determining one or more polysomnography parameters of the subject over time during the sleep session based on the output signals;

means for detecting changes in the cardiorespiratory parameters over time that are indicative of onset of slow wave sleep in the subject, wherein the one or more polysomnography parameters include heart rhythm (ECG and/or EKG), eye movement (EOG), or skeletal muscle activation (EMG) parameters;

means for predicting an upcoming onset time of slow wave sleep in the subject based on the detected changes in the cardiorespiratory parameters; and means for detecting slow wave sleep in the subject based on the predicted upcoming onset time of slow wave sleep and the polysomnography parameters, wherein the detecting is more sensitive during a period of time following the predicted upcoming onset time of slow wave sleep.

14. The system of claim 13, wherein detecting slow wave sleep in the subject based on the predicted upcoming onset time of slow wave sleep and the polysomnography parameters includes enabling detection during the period of time following the predicted upcoming onset time of slow wave sleep.

15. The system of claim 13, wherein the upcoming onset time is a time delay between a time the changes in the cardiorespiratory parameters that are indicative of onset of slow wave sleep in the subject are detected and a time slow wave sleep occurs in the subject.

* * * * *